May 1, 1962 G. MERRILL Plant Pat. 2,145

NECTARINE TREE

Filed May 1, 1961

WITNESS

Addison E. Avery

INVENTOR

GRANT MERRILL

HUEBNER & WORREL

ATTORNEYS

BY Richard M. Worrel

United States Patent Office

Plant Pat. 2,145
Patented May 1, 1962

2,145
NECTARINE TREE

Grant Merrill, P.O. Box 392, Red Bluff, Calif.

Filed May 1, 1961, Ser. No. 106,989
1 Claim. (Cl. 47—62)

The present invention relates to a nectarine tree and more particularly to a new and distinct variety thereof broadly characterized by bearing finely flavored, very highly colored, yellow-fleshed nectarines, which cling to the pits, except when ripened off the tree when there is some tendency toward freeing from the pit, and ripening verly early, and with a vigorous and productive tree.

Because of the rich soil and favorable climatic environment prevailing in most of the commercial nectarine farming areas of California, the nectarine trees tend to produce rank growth and dense shade resulting in serious impairment of the coloring of the fruit. Inasmuch as most fruits rely on eye appeal for their sales, color impairment is highly undesirable.

A primary object of the plant breeding procedures which have resulted in the development of this new nectarine variety has been to achieve a highly colored red nectarine which maintains its color and firmness even under conditions of rank growth and dense shade.

Another object has been to provide an improved early ripening nectarine tree.

Another object has been to provide a nectarine tree somewhat similar to the Merrill Sunrise (Plant Patent No. 1,256) but productive of fruit of brighter red color and of improved flavor.

Further objects and advantages will become apparent in the subsequent description in the specification.

In the drawing which is a water color painting:

Figure 1:
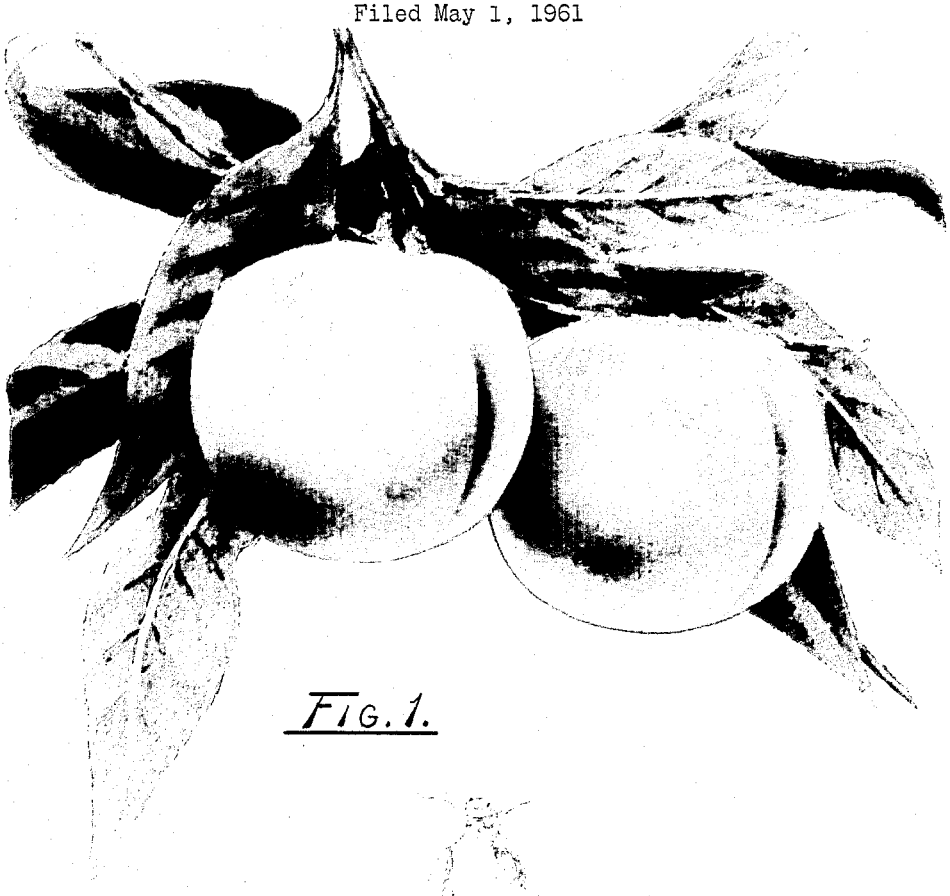
FIG. 1 shows a characteristic fruit bearing twig of the subject nectarine tree showing leaves and mature fruit thereon.
Figure 2:
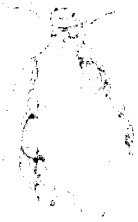
FIG. 2 shows a characteristic fruit of the present variety divided on its suture plane to reveal flesh coloration and flesh partially freed from the stone.
Figure 3:
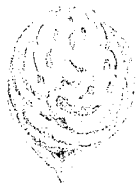
FIG. 3 shows a characteristic stone colored as it appears after drying.

The most distinctive characteristics of the instant variety of nectarine tree is that its fruit has a brilliant red color, fine flavor and ripens very early.

The instant variety most nearly resembles Merrill Sunrise nectarine (Plant Patent No. 1,256) of the known varieties, but is an improvement thereon in that the skin is a more brilliant red with fewer speckles and does not have the brownish-red of the Merrill Sunrise. It is also somewhat sweeter and better flavored, and is a little more free from the pit when ripened off the tree.

The new variety of nectarine tree was produced by me on my breeding farm near Red Bluff, Tehama County, California, from embryo cultured seeds of open pollinated blossoms of Merrill Sunrise nectarine (Plant Patent No. 1,256). I have asexually propagated it on my virus isolation plot at Corning, Tehama County, California, by budding scions of the new variety into host trees. The resulting trees were cared for and when they came into bearing were found to possess the same tree and fruit characteristics as the original tree from which the scions were taken.

Referring more specifically to the pomological characteristics of this new and distinct variety of nectarine tree, the following have been observed under the ecological conditions prevailing at my isolation plot near Corning, Tehama County, California. All major color plate identifications are by reference to Maerz and Paul Dictionary of Color.

*Tree*

Shape: Large, vigorous, medium upright, vase form by pruning, productive and regular bearing.

Trunk: Medium stock, medium shaggy, brownish grey color. Lenticels—numerous large.

Leaves (selected from midportion of vigorous unbranched terminal shoot 18" to 24" long):

*Length.*—4 3/16" to 5 1/4".

*Width.*—1 1/16" to 1 3/16".

*Form.*—Medium size, lanceolate, tip acuminate, medium thick.

*Color.*—Upper surface, dark green (22–L–7). Under surface medium green (22–K–5). Midrib on under side, yellow green (18–K–2).

*Class* (Meader and Blade Proceedings: Am. Soc. Hor. Sc., vol. 37, page 206).—Class 2. Width to length ratio—.28 to .35. Apex angle (1" from tip)—40°. Base angle (½" from petiole)—60° to 80°.

*Margin.*—Crenate.

*Petiole.*—Medium length, medium slender.

*Stipules.*—Appear on young leaves dropping off early.

*Glands.*—None to six, mostly 2. Alternate, medium size, reniform, greenish in color.

Flower buds: Plump, free, pubescent.

Flowers: Medium late, about the same season as Merrill Sunrise (Plant Patent No. 1,256), large, pink, showy.

*Anthers.*—Yellow to orange.

*Pollen.*—Abundant.

*Fruit*

Maturity when described, firm ripe, approximately June 20 to June 25.

Size: Medium.

*Axial diameter.*—2" to 2 1/4".

*Transverse in suture plane.*—2 1/8" to 2 5/16".

*At right angles to suture plane.*—2 1/8" to 2 3/8".

Form: Symmetrical, globose.

*Suture.*—Distinct, an inconspicuous line over the entire circumference, with marked depression beyond pistil point.

*Ventral surface.*—Strongly lipped on either side. Lips equal.

*Cavity.*—Rounded, suture showing on both sides. Depth, 1/4"; width, ½" to 1".

*Base.*—Truncate.

*Apex.*—Rounded.

*Pistil point.*—Generally not present, but apical when present.

Stem: Length.—1/8" to 3/16".

*Diameter.*—3/16" to 1/4".

*Adherence to stone.*—Seldom.

Skin: Medium thick, medium tender, tenacious to flesh.

*Tendency to crack.*—Little.

*Color.*—Undercolor, generally reddish-orange (3–A–12) with some yellow green (17–L–3) near the stem end. Spotted and striped with red (4–L–7) to (5–K–11). Dark red (4–L–6) to (7–L–8) when exposed to sun.

*Down.*—Wanting.

Flesh: *Color.*—From light golden yellow (9–L–2) to orange-yellow (9–L–6) and deepening on the side most exposed to the sun to reddish-orange (9–A–10).

*Amygdalin.*—Moderate.

*Juice.*—Rich, abundant.

*Texture.*—Medium.

*Fibers.*—Fine.

*Ripens.*—Evenly.

*Flavor.*—Subacid, mild.

*Aroma.*—Distinct.

*Eating quality.*—Good.

Stone: Adheres to flesh when firm ripe, but frees slightly when ripened off the tree.

*Fibers.*—Short.

*Size.*—Length, 1⅛″ to 1⅜″; breadth, 15/16″ to 1⅛″; thickness, ¾″ to 15/16″.

*Form.*—Elliptical to ovoid, with some tendency toward cuneate toward base.

*Base.*—Oblique.

*Hilum.*—Oval.

*Apex.*—Acute.

*Sides.*—Unequal, flattened on either side.

*Surface.*—Irregularly furrowed throughout, ridged on the ventral side, pitted throughout, ridges rounded toward apex. Pits usually elongated, sometimes round.

*Ventral edge.*—Without wing.

*Dorsal edge.*—With deep groove throughout.

*Color.*—When released from flesh—a dark-orange (5–C–11); when allowed to dry—tan (9–C–4).

*Tendency to split.*—None.

*Use*: Market, local, dessert, long distance shipping.

Keeping quality: Good.

Shipping quality: Good.

Although the new variety of nectarine tree possesses the described characteristics under the growing conditions prevailing throughout most of the commercial nectarine producing areas of California, having been first observed near Red Bluff, California at the northern end of the Sacramento Valley and later confirmed by observation of the same variety at Corning, Tehama County, California, it is to be understood that variations of the usual magnitude in characteristics incident to growing conditions, fertilizing, pruning, thinning and pest control are to be be expected.

Having thus described my new nectarine tree, what is claimed as new and desired to be secured by Letters Patent is:

A new and distinct variety of nectarine tree, substantially as illustrated and described, characterized by a vigorous and productive tree having highly colored, early ripening fruit, with finely flavored yellow flesh that frees from the stone when ripened off the tree and which ripens with the Merrill Sunrise nectarine (Plant Patent No. 1,256), the variety to which it is the most similar but which is an improvement thereof in having skin of brighter red color and fewer speckles, and flesh which is sweeter, better flavored and somewhat more free from the pit when ripened off the tree.

No references cited.